United States Patent [19]

Mimken et al.

[11] Patent Number: 5,744,716
[45] Date of Patent: Apr. 28, 1998

[54] FLUID DISPLACEMENT LEVEL, DENSITY AND CONCENTRATION MEASUREMENT SYSTEM

[75] Inventors: Victor B. Mimken; Sergey A. Velichko; Tom Krawzak, all of Boise, Id.

[73] Assignee: SCP Global Technologies, a division of PRECO, Inc., Boise, Id.

[21] Appl. No.: 660,642

[22] Filed: Jun. 7, 1996

Related U.S. Application Data

[60] Provisional application No. 60/000,041, Jun. 8, 1995.

[51] Int. Cl.⁶ ............................................. G01N 9/12
[52] U.S. Cl. .......................... 73/453; 73/61.51; 73/309
[58] Field of Search ............................. 73/61.51, 451, 73/452, 453, 454, 309, 306, 307, 308; 340/624, 625

[56] References Cited

U.S. PATENT DOCUMENTS

| | | | |
|---|---|---|---|
| 2,038,273 | 4/1936 | Eynon | 73/309 |
| 2,460,503 | 2/1949 | Howe | 73/453 |
| 3,089,502 | 5/1963 | Davidson et al. | 73/453 |
| 4,244,218 | 1/1981 | Wohrl | 73/309 |
| 5,157,968 | 10/1992 | Zfira | 73/433 |
| 5,277,054 | 1/1994 | Campbell | 73/1 H |

*Primary Examiner*—John E. Chapman
*Attorney, Agent, or Firm*—Limbach & Limbach LLP

[57] ABSTRACT

A method and apparatus for monitoring characteristics of a fluid contained in a vessel includes a pair of triangular fluid displacers suspended in the vessel. The buoyant forces acting on the fluid displacers are measured using force transducers and used to calculate fluid characteristics such as the height of the fluid in the vessel, fluid density, solute concentration, and/or the presence of fluid cascading from one section of the vessel to another.

21 Claims, 7 Drawing Sheets

FLUID DISPLACEMENT LEVEL, DENSITY AND CONCENTRATION MEASUREMENT SYSTEM

REFERENCE TO RELATED APPLICATIONS

This patent application is a non-provisional application filed under 35 U.S.C. §111(a) claiming priority under 35 U.S.C. §119(e)(1) based on 60/000,041, filed Jun. 8, 1995, the full text of which is incorporated herein by reference.

FIELD OF THE INVENTION

This invention relates to a fluid parameter monitoring device of the type useful in wet-etch processing of silicon wafers, wherein it is essential that the fluid height in a processing vessel remains at a level sufficient to completely cover the wafers.

BACKGROUND OF THE INVENTION

In the wet-etch processing of silicon wafers, it is essential that the wafers remain fully covered by the etching solution during the course of the process. Should the liquid level in the process tank fall below the uppermost surface of the wafers, the extent of etching will vary over the wafers' surface. The resulting inhomogenously etched product will be of unacceptably low quality.

Avoiding incomplete etching of the wafers is also important from an economic standpoint. For example, in a typical wet-etch processing cycle, over one million dollars in silicon wafers are in the wet-etch bath at any given time. Clearly, having to dispose of a batch of inhomogenously etched wafers represents a significant waste of financial and material resources.

Thus, it is desirable from both product quality and economic standpoints to continuously monitor the fluid height of the etching solution in a process vessel to ensure that it remains above the upper surface of the silicon wafers and does not drop below a minimum level.

During the wet-etch process, the etching solution in the process vessel is continuously recirculated between an inner and outer weir of the vessel. The silicon wafers are processed in the inner weir and the outer weir serves as a reservoir for the etching solution.

Recirculation of the etching solution is essentially a two step process. The solution is transferred from the outer weir into the inner weir by means of a pump. During this transfer, the etching solution flows continuously over the top edge of the inner weir of the vessel and back into the outer weir. The process of the etching solution flowing from the inner weir into the outer weir is known as fluid cascading. The integrity of the recirculation process can be ensured by monitoring for the presence of cascading fluid.

Due to the caustic nature and cost of the etching solutions it is important to control the rate of cascading to minimize the danger of spillage. Further, the absence of cascading, caused by a lower than optimum fluid level, risks damage to the pumps used to recirculate the etching solution. Thus, in a wet-etch processing tank, it is advantageous to monitor both fluid level and solution cascading.

Fluid height monitoring devices which have been used in chemical process tanks include gas bubblers, optical cells, and sonic and radiofrequency devices.

A fluid parameter monitor for wet-etch processing tanks must be stable over a wide range of conditions. The wet etch chemical process solutions are dynamic and characteristically in motion. The solutions are typically heated and, as mentioned above, are constantly recirculated. The dynamic environment in the process tank is further complicated by the presence of bubbles in the solution. Additionally, changes in solution temperature, density and solute concentration will affect the fluid height and the device used to measure it.

Many of the prior art fluid parameter monitoring systems are simply unable to function with the requisite accuracy in an environment such as a wet-etch processing tank. For example, the presence of bubbles in the solution makes optical and sonic monitoring devices virtually nonfunctional. Although gas bubblers can be used in wet-etch process tanks their use necessitates the addition of a foreign substance into the process tank and thus risks contaminating the processing solution. Moreover, gas bubblers take fluid level measurements at discrete levels rather than continuously at all fluid levels.

Other fluid height measuring devices are known. For example, a method and apparatus for measuring the height of a fluid of constant density is disclosed in U.S. Pat. No. 5,277,054. The '054 patent discloses fluid height measurement as useful for determining a calibration constant for the in-situ calibration of distance measuring equipment. The disclosed method utilizes the difference in pressure between two different regions of a displacer of known length to measure fluid height. The apparatus is comprised of a single fluid displacer coupled to a pressure transducer.

The dynamic nature of the solution in the process tank makes it desirable to simultaneously measure more than one changing fluid parameter. For example, as the temperature of the wet-etch solution changes the solution's density will also change. As the fluid density changes, the buoyant forces on the fluid displacer, and thus its suspended weight will be altered. Unless the change in density is compensated for, inaccuracies in the measurement of fluid height will develop.

In view of the above, it is an object of the present invention to provide a fluid parameter monitoring system which is capable of continuously and simultaneously monitoring multiple fluid parameters such as fluid height and density, which is stable over a wide range of fluid conditions, and which is accurate. It is a further object of the present invention to utilize fluid displacers and other components which are unlikely to contaminate the process solution with foreign substances.

SUMMARY OF THE INVENTION

The present invention provides a method and an apparatus for accurately monitoring at least one parameter of a fluid contained in a vessel. Monitored parameters may include fluid height, density, solute concentration and/or the presence of cascading fluid.

The method comprises the steps of measuring fluid forces acting upon a fluid displacer suspended in a fluid-containing vessel and subsequently converting the fluid forces into a fluid characteristic such as fluid level, fluid density, solute concentration and/or a signal indicating the presence of cascading fluid. The measured fluid forces are typically the buoyant forces imparted against the displacers by the fluid in the vessel.

The apparatus of the invention is a device for measuring the forces acting on at least one fluid displacer and converting the forces into a fluid parameter such as fluid height, density, solute concentration and/or a signal indicating the presence of cascading fluid.

In a first embodiment the apparatus of the invention is a device for measuring the buoyant forces acting on at least one fluid displacer suspended in a fluid vessel and for converting the measured buoyant forces to a fluid parameter or characteristic. The fluid displacer is shaped such that the buoyant forces acting upon the displacer can be described by a mathematical equation. For example, the displacer may be triangular (the term "triangular" is intended to include all forms of triangles, including isosceles, acute, and right triangles, as well as trapezial, or trapezoidal displacers), or it may have a parallelogram shape or a constant cross-section.

A force transducer is coupled to the fluid displacer, and a processor or other means is coupled to the force transducer for receiving a first value representing the buoyant forces acting on the fluid displacer and converting the first value to a second value representing a fluid characteristic or parameter. The second value determined by the processor may represent fluid parameters such as fluid height, fluid density, and solute concentration and/or the presence of cascading fluid.

One of the fluid displacers may be suspended in the vessel at a location at which cascading is to occur from a first section in the vessel to a second section of the vessel. A buoyant force transducer coupled to this displacer may be used to determine whether the fluid level in the first section of the vessel is sufficiently high for liquid to cascade into the second section.

BRIEF DESCRIPTION OF THE DRAWINGS

The present invention will be better understood by reference to the appended drawing figures, of which.

DETAILED DESCRIPTION OF THE INVENTION

The present invention provides an effective method and device for simultaneously monitoring several parameters of a fluid contained within a vessel. Specifically, the present invention is capable of accurately monitoring parameters such as fluid level, density, the presence of fluid cascading from one region of the vessel to another, and solute concentration. An exemplary application of the invention will be for monitoring fluid parameters in wet-etch chemical process tanks.

The figures depict only a few embodiments of this invention, although it should be understood that many other embodiments may be configured within the scope of the present invention. Throughout this specification monitoring fluid parameters in wet-etch chemical process tanks will serve as an illustration of the use of this invention, though the invention can be used to monitor fluid parameters in any liquid containing vessel.

Figure 1:
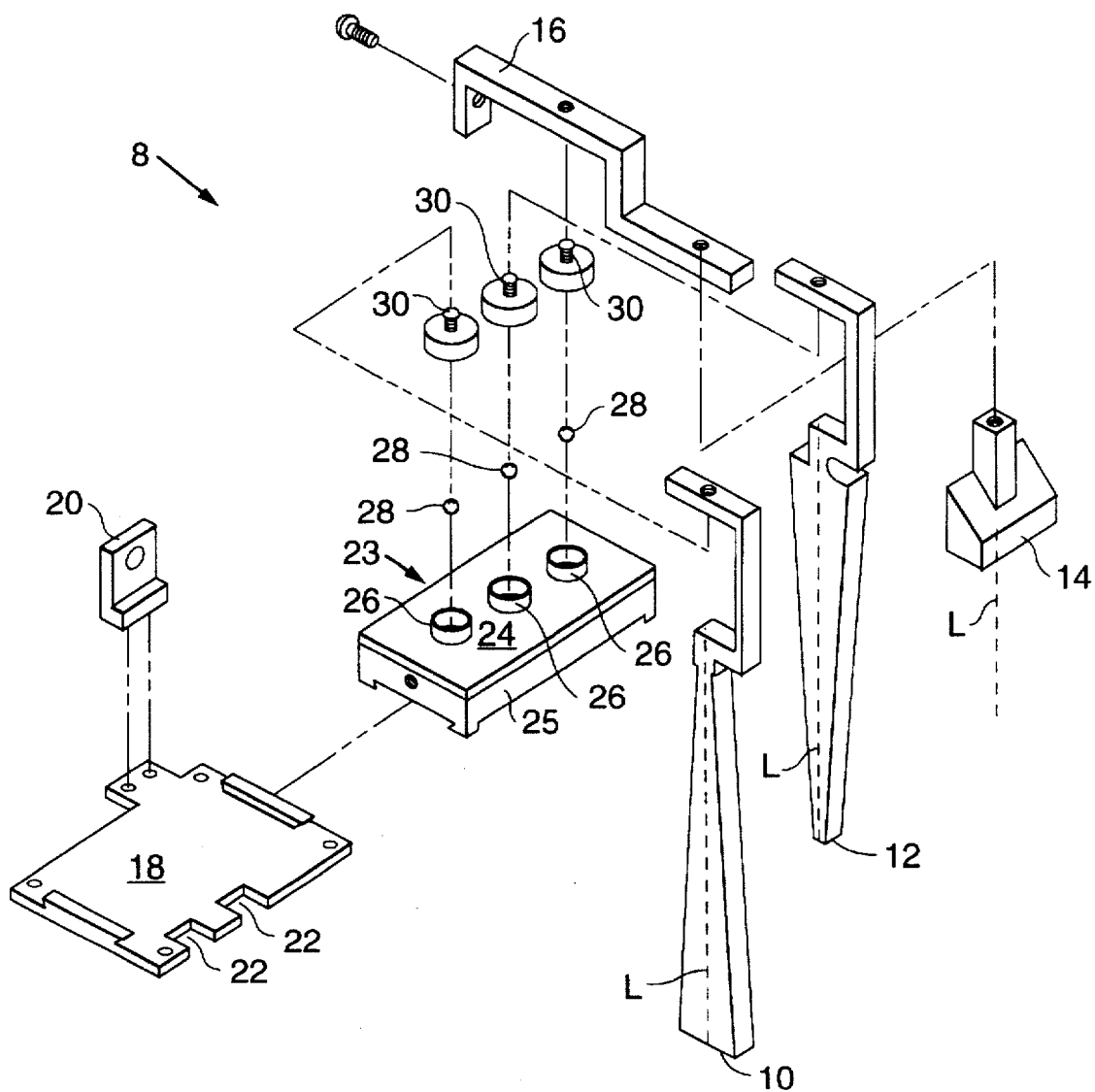
FIG. 1 is an exploded perspective view of a preferred fluid parameter measuring system according to the present invention; utilizing two triangle-shaped displacers and one constant cross-sectional displacer.

FIG. 1 is an exploded perspective view of the components of the preferred fluid parameter monitoring apparatus 8 of the invention. Fluid parameter monitoring apparatus 8 is made up of an upright triangular wedge-shaped fluid displacer 10, an inverted triangular wedge-shaped fluid displacer 12 and an arbitrarily shaped fluid displacer 14. The displacers may have any shape, although the displacers 10, 12 should have shapes that are different from one another (or, if their shapes are the same, their orientation should differ) so that different buoyant force equations may be generated for each of the displacers 10 and 12.

The preferred fluid displacers are made of the same inert material as the processing tank; typically, Teflon®, quartz, stainless steel, etc. The fluid displacers are shaped such that the buoyant forces acting on the fluid displacers when they are immersed in a fluid are amenable to description by two simultaneous mathematical equations.

The displacer 14 may have any shape, including an irregular shape. However, it is preferable that displacer 14 have a shape of constant cross-section because displacers having constant cross-sections experience a buoyant force (imparted on them by the fluid in which they are immersed) which is linear with fluid height. Thus, fluid height may be more easily expressed as a function of buoyant force when a displacer 14 of constant cross-sectional area is used.

Figure 8:
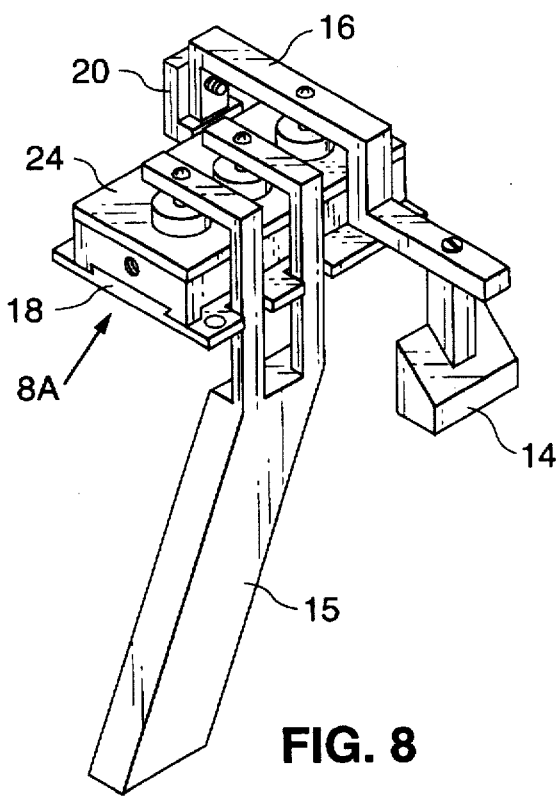
FIG. 8 is a perspective view of an alternative fluid parameter measuring system according to the present invention, which utilizes a parallelogram-shaped displacer and a constant cross-sectional fluid displacer.

Fluid displacer 14 is attached to a support beam 16 which is affixed to a transducer housing support plate 18 by means of bracket 20 (see also FIG. 8).

The transducer housing support plate 18 is inscribed with notches 22 which serve as positioning guides for the triangular wedge-shaped fluid displacers 10 and 12, thus minimizing the transverse motion of these fluid displacers. In operation, the triangular wedge-shaped displacers 10, 12 are preferably used to monitor two fluid parameters: fluid level and fluid density. As will be discussed with reference to FIGS. 6 and 7, the third displacer, 14 is used to monitor for the presence of cascading fluid, i.e., the overflow of fluid from an inner weir into an outer weir of a wet-etch process tank.

Still referring to FIG. 1, transducer housing assembly 23 includes a transducer housing lid 24 mounted on a transducer housing base 25 which is attached to the transducer housing support plate 18. Transducer housing lid 24 includes three openings 26. A fluid displacer pivot 28 is mounted within each opening. Engaging each of the fluid displacer pivots 28 is a fluid displacer seat 30. Fluid displacers 10, 12 and 14 are mounted on respective ones of the fluid displacer seats 30. Preferably, triangular displacers 10, 12 and support beam 16 are mounted to three of the seats 30 such that the each seat 30 lies within the longitudinal axis 1 of its respective displacer. Each fluid displacer seat 30 is in turn coupled to one of the displacer pivots 28.

Figure 2:
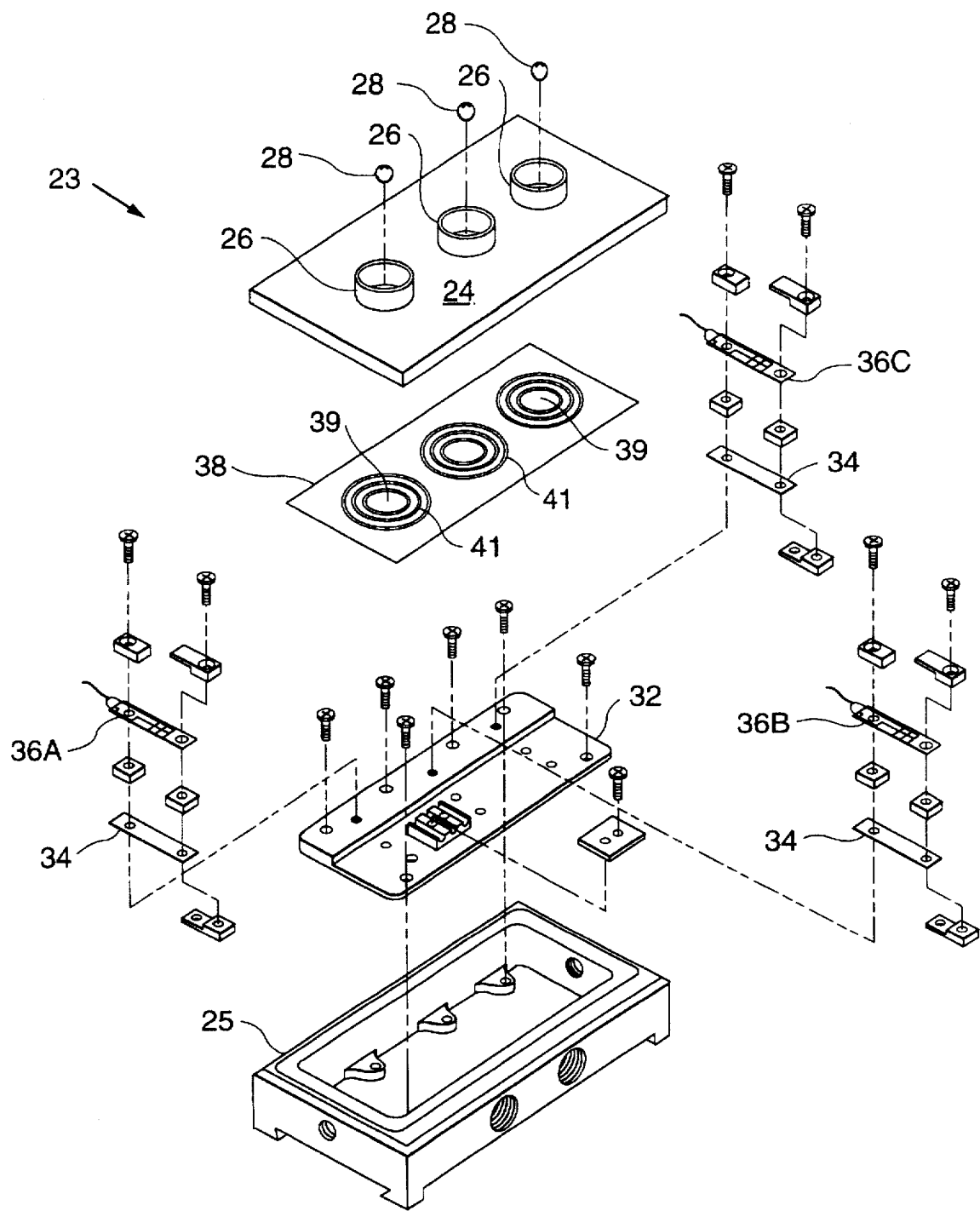
FIG. 2 is an exploded perspective view of the transducer housing assembly of the preferred embodiment.

In all figures herein, including FIG. 2, like fluid parameter monitoring apparatus components are numbered as in FIG. 1.

FIG. 2 is an exploded perspective view of the transducer housing assembly 23 of the preferred embodiment. Referring to FIG. 2, the transducer housing assembly 23 includes transducer housing base 25 and lid 24. A transducer mounting plate 32 is mounted within the base 25, and springs 34 are fastened to the plate 32. Transducers 36a, 36b, 36c are mounted to the springs 34 such that the springs are positioned between the transducers 36a, 36b, 36c and the transducer mounting plate 32.

A preferred transducer is a Revere Transducers Model 801 Planar Beam sensor with a 0.5 pound capacity, although other force transducers including tension, compression, and bending beam style load cells are also suitable for use in the invention. The transducer capacity may be varied depending on the weight and volume of the displacers.

The preferred embodiment further comprises a chemical isolation diaphragm 38 positioned between the transducer housing base 25 and the transducer housing lid 24. In operation, the chemical isolation diaphragm 38 serves as a liquid tight seal between the outside environment and the interior of the transducer housing assembly 23. The diaphragm is preferably formed of 0.002 inch thick Teflon®. It includes three regions 39 each of which is surrounded by concentric rings 41 pressed into the Teflon®. This convolution in the diaphragm reduces its stiffness at the regions 39 and prevents the diaphragm from having an appreciable influence on the buoyant force measurements made by the system.

Fluid displacer pivots 28, mounted within openings 26, rest on the chemical isolation diaphragm 38.

Figure 3:
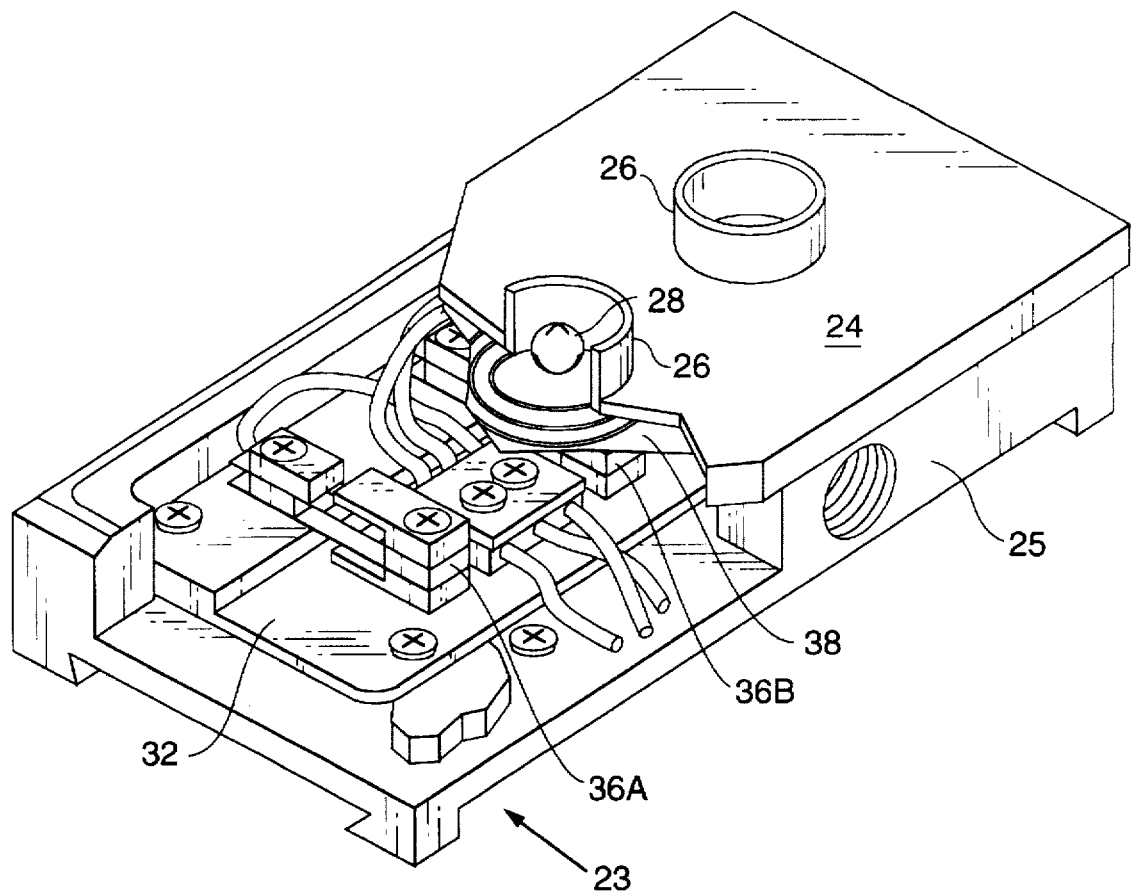
FIG. 3 is a partial cross-sectional view of the fully assembled transducer assembly of the preferred embodiment.

FIG. 3 is a partial cross-sectional view of the assembled transducer assembly 23 of the preferred embodiment which illustrates the relative positions of the transducer assembly components when the transducer assembly is fully assembled. As shown, transducer mounting plate 32 is attached to the transducer housing base 25. The chemical isolation diaphragm 38 is interleaved between the transducer housing base 25 and lid 24. The fluid displacer pivots 28 (only one shown in FIG. 3) are mounted within the openings 26 and rest on the chemical isolation diaphragm 38.

Figure 6:
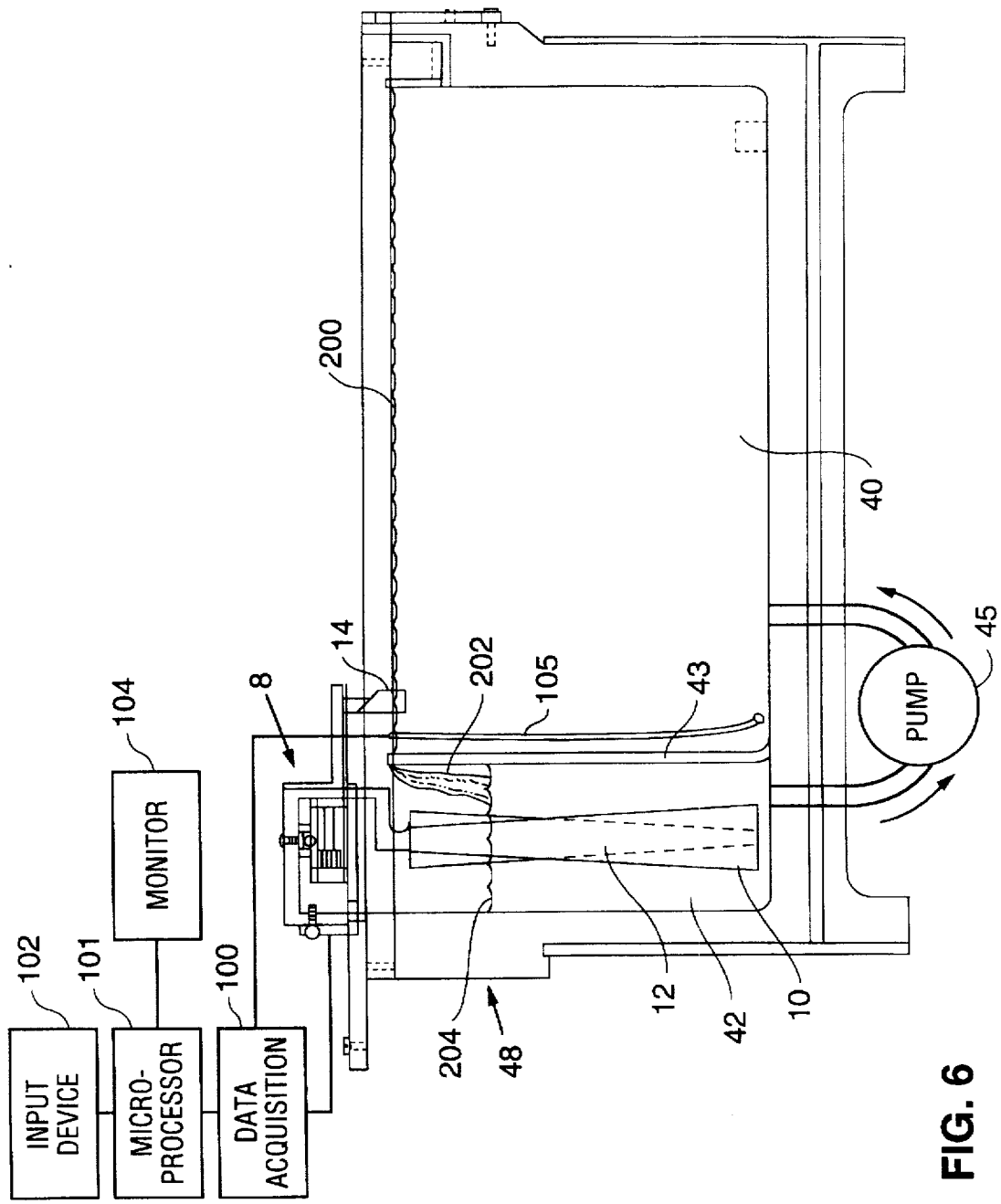
FIG. 6 is a cross-sectional side view of the fluid parameter measuring system of FIG. 1 as used in a wet-etch process tank.
Figure 7:
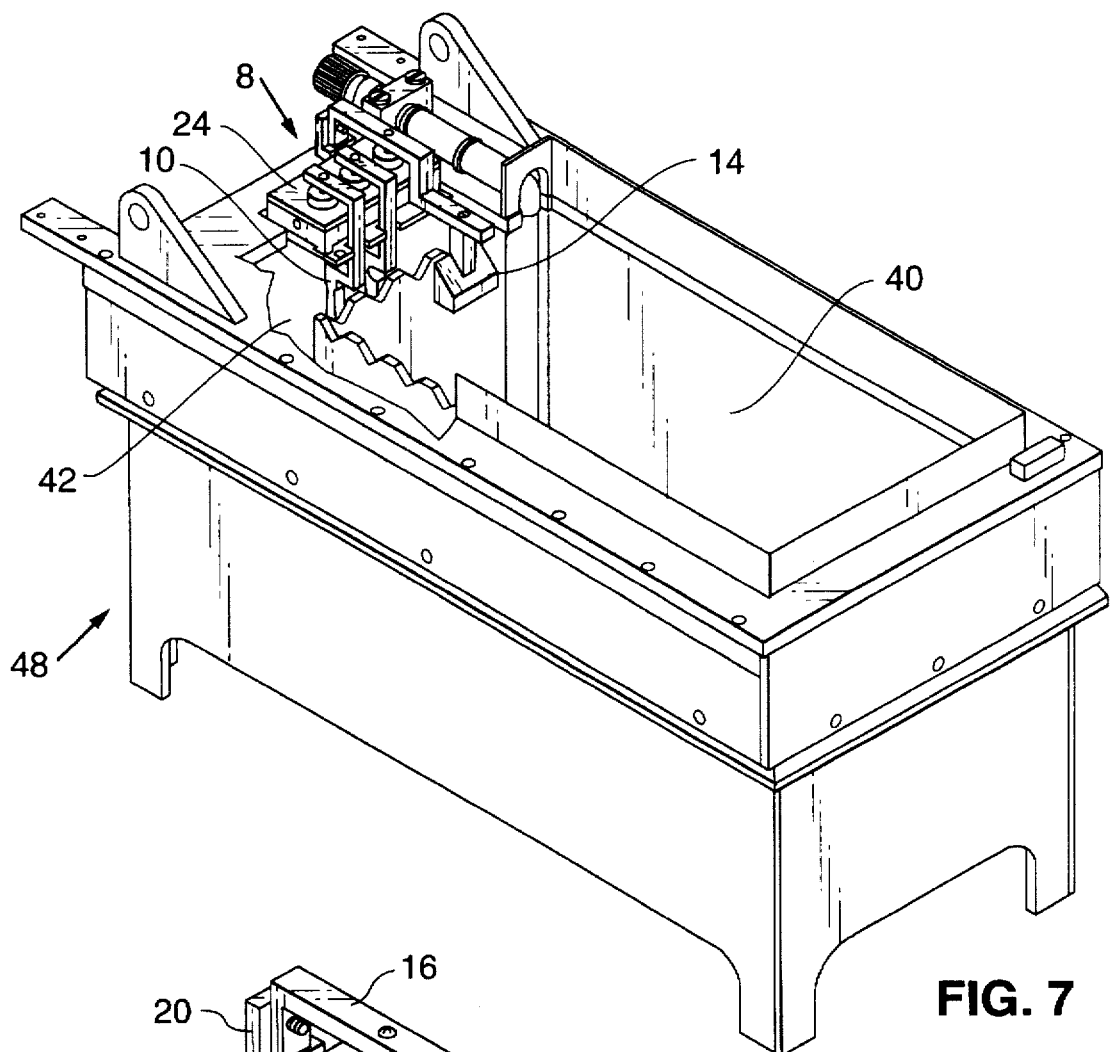
FIG. 7 is a perspective view of the fluid parameter measuring system of FIG. 1 as used in a wet-etch process tank. For clarity, a portion of the tank has been cut away.

FIGS. 6 and 7 show the preferred fluid parameter measuring system 8 as used in a wet-etch process tank 48 which includes an inner weir 40 and an outer weir 42 separated by wall 43. Outer weir 42 contains a processing fluid. The triangular displacers 10 and 12 are submerged in the fluid contained in the outer weir 42. Fluid displacer 14 is positioned to detect the presence of fluid cascading over the wall 43 from the inner weir 40 to the outer weir 42 by determining whether the liquid level in inner weir 40 is of a sufficient height to cause fluid to cascade over wall 43. A pump 45 pumps fluid from outer weir 42 to inner weir 40.

A data acquisition system 100 (FIG. 6) is electronically coupled to the transducers 36a, 36b, 36c and receives signals from the transducers 36a, 36b corresponding to the buoyant forces acting on the displacers 10, 12. The data acquisition system 100 further receives signals from the transducer 36c indicating whether displacer 14 is being subjected to buoyant forces imparted against it by fluid cascading from the inner weir 40 to the outer weir 42. The data acquisition system 100 also receives signals from a temperature probe 105 or other temperature monitoring device suspended in the inner weir. These signals correspond to the temperature of the fluid and are used to determine solute concentration.

Data acquisition system 100 includes conventional electronic components such as an amplifiers, analog filters, multiplexers, and an analog to digital converter. A microprocessor 101 is electronically coupled to the data acquisition system for receiving signals from the data acquisition system corresponding to the buoyant forces on the displacers 10, 12 and 14 and for using those values to determine fluid height and density.

As discussed, the fluid displacers 10, 12 are shaped such that the buoyant forces acting on the fluid displacers are amenable to description by two simultaneous mathematical equations. The solution of the two simultaneous equations allows fluid height and density to be monitored simultaneously. During use, the microprocessor 101 utilizes these equations and the buoyant forces measured by the transducers 36a, 36b (FIG. 2) to determine the desired fluid parameters. The microprocessor further utilizes signals representing temperature measured by probe 105 to determine the concentration of the solute. The microprocessor 101 is preferably coupled to an input device 102 such as a keypad which allows a user to select the desired fluid parameters and which delivers the user commands to the microprocessor 101, and an output device 104 such as a monitor which displays the fluid parameters calculated by the microprocessor 101.

The method by which the microprocessor determines fluid characteristics such as fluid level, density, and solute concentration using the preferred embodiment of the invention will next be described.

Figure 4A:
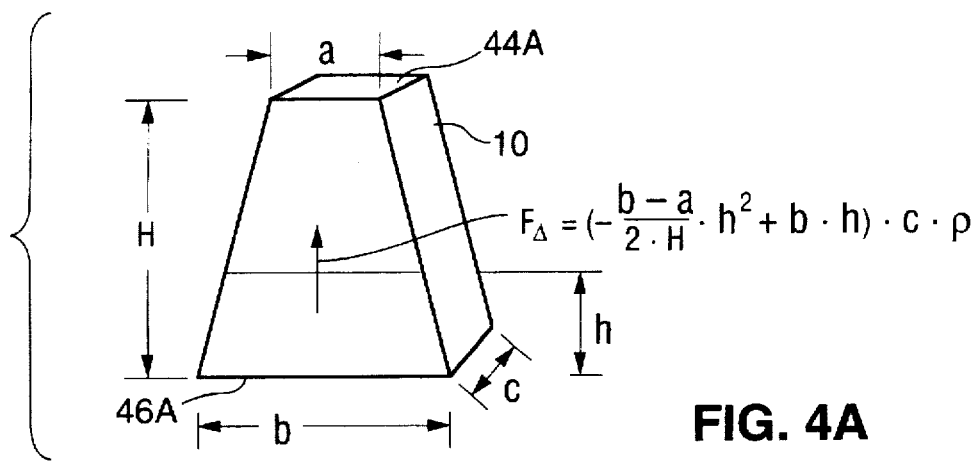
FIGS. 4A and 4B are diagrams showing the buoyant forces acting on an upright triangular shaped displacer and an inverted triangular shaped displacer, respectively, when such displacers are submerged in a fluid. The equations used to describe the forces are also shown.
Figure 4B:
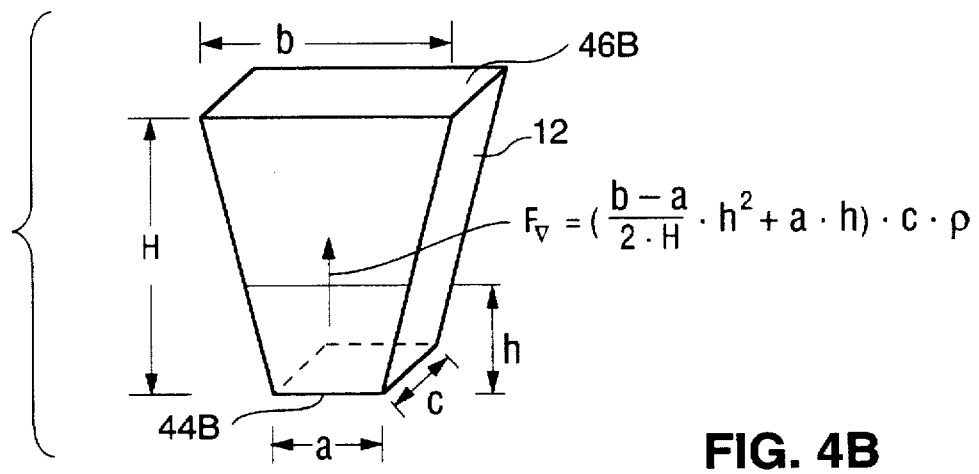

FIGS. 4A and 4B illustrate the respective buoyant forces $F_\Delta$ and $F_\nabla$ operating on upright and inverted wedge-shaped displacers 10, 12, respectively, when they are submerged in a fluid. These forces are measured by transducers 36a, 36b and signals representing the forces are delivered to the microprocessor 101.

Each wedge-shaped displacer includes a rectangular small face 44a, 44b of width a and depth c. Each triangular displacer also has a rectangular large face 46a, 46b which is of width b and depth c. The upright wedge-shaped fluid displacer 10 enters a fluid via its large face 46a. In contrast, the inverted wedge-shaped displacer enters a fluid with its small face 44b entering the fluid first. H is the height of each displacer, i.e., the distance between faces 44a, 44b and 46a, 46b. The height to which the fluid rises on each displacer is represented by h.

The equations shown in FIGS. 4A and 4B representing the buoyant forces operating on the wedge-shaped and inverted wedge-shaped fluid displacers 10, 12 are simultaneously solved to obtain a formula for the fluid height h. Thus, $$h = H \cdot \left( 1 - \frac{a+b}{b-a} \cdot \frac{F_\Delta - F_\nabla}{F_\Delta + F_\nabla} \right) \qquad (1)$$

The fluid height h may therefore be calculated by inserting dimensions a and b of the fluid displacers and the buoyant forces $F_\Delta$ and $F_\nabla$ acting on the triangular wedge-shaped and inverted wedge-shaped displacers, respectively and measured by the transducers 36a, 36b.

Although equation (1) has been found to give highly accurate readings for high fluid levels, it has been found that the accuracy of the system can decrease as fluid height in the tank decreases significantly. A second equation has been developed which provides greater accuracy at lower liquid levels.

Figure 5:
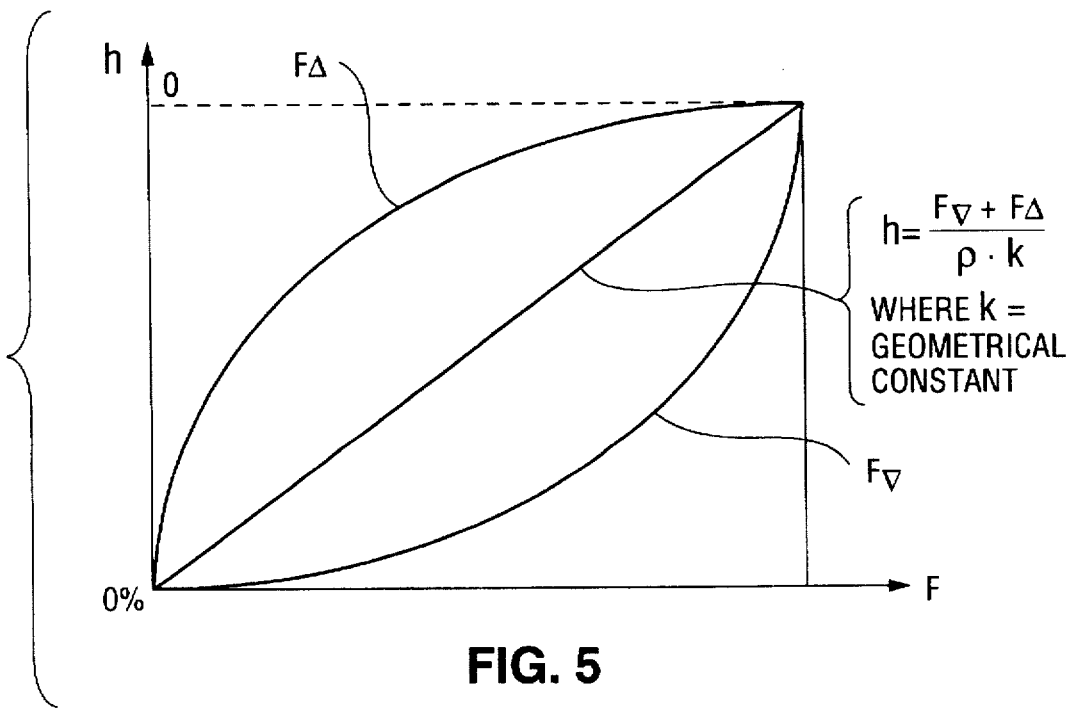
FIG. 5 is a plot of buoyant forces vs. fluid height for the buoyant forces acting on the upright triangular displacer of FIG. 4A and the inverted triangular displacer of FIG. 4B, when submerged in a fluid.

FIG. 5 is a plot of buoyant forces vs. fluid height for the buoyant force $F_\Delta$ acting on an upright triangular displacer such as displacer 10 of FIG. 1 and buoyant force $F_\nabla$ acting on an inverted triangular displacer such as displacer 12 of FIG. 1, when both such displacers are submerged in a fluid.

FIG. 5 demonstrates that fluid height is linear with respect to the sum of the buoyant forces, $F_\Delta$ and $F_\nabla$, acting on the two triangle-shaped displacers. Thus, fluid height can be described by equation (2):

$$h = \frac{F_\Delta + F_\nabla}{c(a+b)\rho g} \quad (2)$$

where $\rho$ is the absolute fluid density, and g is the gravitational constant. Equation (2) allows the preferred embodiment of the invention to accurately measure fluid heights using equation (1) for higher fluid levels and equation (2) for lower fluid levels.

Naturally, the approximate liquid level at which equation (2) becomes more accurate than equation (1) will vary with the system and can be determined experimentally by measuring actual liquid levels and comparing them with levels measured using the system of the present invention. Using the preferred triangular displacers, it was experimentally determined that equation (1) is more accurate for liquid levels greater than 30% and that equation (2) is more accurate for liquid levels below 30% (i.e., where h is less than 30% of displacer height H).

The system further utilizes the measured buoyant forces $F_\Delta$ and $F_\nabla$ to calculate the absolute density of the solution in the tank. Combining equation (1) and equation (2), the following equation can be written for the fluid density $\rho$:

$$\rho = \frac{\frac{F_\Delta + F_\nabla}{cg(a+b)}}{H \cdot \left(1 - \frac{a+b}{b-a} \cdot \frac{F_\Delta - F_\nabla}{F_\Delta + F_\nabla}\right)} \quad (3)$$

It should be noted that while equations (1) and (2) simultaneously solve for fluid height and density, equation (2) solves only for fluid height. Thus, when performing calculations using equation (2) the system utilizes the last density measurement obtained when the system was operating with equation (1) and (2).

Once the temperature of the analyzed fluid has been measured by probe 105 and the density of the fluid has been calculated using equation (3), the concentration of the solute may be obtained by the microprocessor 101 using standard look up tables stored in its memory. Concentrations of up to two combined solutes may be determined provided the solutes have different densities.

Finally, the system determines the presence of cascading fluid by looking at the buoyant force exerted against the displacer 14. Referring to FIG. 6, when the fluid level 200 in inner weir 40 is higher than the wall 43, a fluid cascade 202 passes over the wall 43 from the inner weir 40 to the outer weir 42. The fluid height in the outer weir is designated 204. Because the buoyant force is linear with fluid height, a buoyant force in excess of a certain calculable threshold will be exerted against the displacer 14 when the fluid height has reached or exceeded the height of wall 43. Thus, the system may be programmed to compare the measured buoyant force with a threshold level and to produce an output signal when the buoyant force against displacer 14 exceeds the threshold, indicating that the fluid level in the outer weir 40 has exceeded the level at which cascading begins to occur.

The preferred embodiment of the invention further comprises a conventional analog and/or digital filtration, analog-to-digital conversion, and data calculation method and apparatus for reducing errors from random and periodic noise.

Alternate Displacer Designs

FIG. 8 is a diagram showing a first alternate embodiment of a fluid parameter measuring system 8a according to the present invention wherein a parallelogram-shaped fluid displacer 15 may be used to simultaneously monitor fluid parameters such as fluid height, fluid density and/or solute concentration. With the exception of the shape of the displacer 15, the alternate embodiment utilizes features identical to those described with respect to the preferred embodiment. The description of the first alternate embodiment will therefore focus on the formulas used to determine liquid level, density, and solute concentration using the buoyant forces imparted by the fluid on the displacer 15 and measured by the transducers coupled to the displacer 15.

Figure 9:
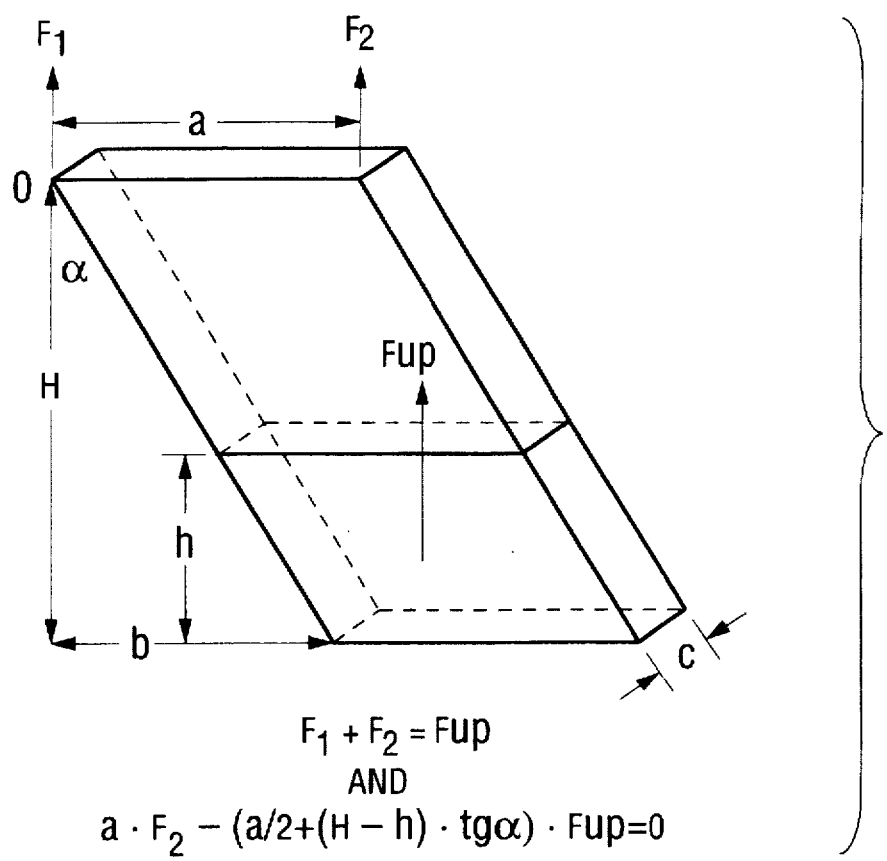
FIG. 9 is a diagram showing the forces acting on the parallelogram shaped displacer of the embodiment of FIG. 8 when submerged in a fluid, and further showing the equations used to describe those forces.

FIG. 9 is a diagram showing the buoyant forces acting on a parallelogram shaped displacer submerged in a fluid. In FIG. 9, $F_{up}$ is the upward buoyant force on the fluid displacer. $F_1$ and $F_2$ comprise the force couple generated by $F_{up}$. a, b, H are the geometrical parameters of the displacer and $tg\alpha=b/a$. Height h is equal to the height of the fluid on the displacer.

Still referring to FIG. 9, the equations used to calculate the buoyant forces operating on the parallelogram-shaped fluid displacer are combined by substituting the sum of $F_1$ and $F_2$ for $F_{up}$ and taking into account that $tg\alpha=b/a$, the resulting equation solved for the fluid height is, $$h = H \cdot \left(1 - \frac{a}{2b} \cdot \frac{F_2 - F_1}{F_1 + F_2}\right) \quad (4)$$

Thus, by measuring $F_1$ and $F_2$ and knowing the geometric parameters of the displacer it is possible to calculate fluid height.

As with the preferred embodiment, when the parallelogram-shaped displacer is used there is a decrease in accuracy as fluid height decreases. Thus, a second equation has been developed for use with the parallelogram shaped when the fluid height falls below a predetermined level which may be experimentally determined as described above. This equation, equation (5) defines the measured fluid height as being linear with respect to the sum of F1 and F2:

$$h = \frac{F_1 + F_2}{a \cdot c \cdot \rho g} \quad (5)$$

where g is the gravitational constant. Combining equations (4) and (5), gives an equation for the density of the fluid, using a parallelogram shaped displacer:

$$\rho = \frac{\frac{F_1 + F_2}{(a \cdot c)g}}{H \cdot \left(1 - \frac{a}{2 \cdot b} \cdot \frac{F_2 - F_1}{F_1 + F_2}\right)} \quad (6)$$

Similar to equation (2), equation (5) allows lower fluid heights (i.e., those falling below the experimentally determined level) to be accurately measured. As described above, the calculated density may be used with the measured temperature to determine solute concentration from a look up table stored in the memory of the microprocessor.

As discussed, the fluid displacers 10, 12, 14 may be provided to have any shape (be it regular, irregular, or arbitrary), although shapes such as those described above which facilitate mathematical expression of buoyant force, fluid height, and density are preferred.

Figure 10:
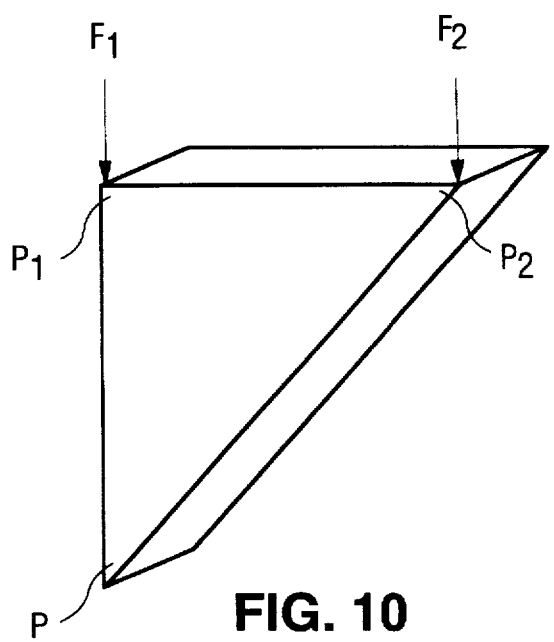
FIG. 10 is a perspective view of an alternative triangular fluid displacer illustrating reaction forces acting on the displacer when it is submerged in a fluid and further showing the equations used to describe those forces.

A second alternate displacer 15a is shown in FIG. 10. With the exception of the shape of the displacer 15a, the second alternate embodiment utilizes features identical to those described with respect to the preferred embodiment.

Displacer 15a is a right triangular displacer, although a displacer of any triangular shape which is assymetrical along the vertical line may be used. During use, displacer 15a is preferably suspended in a vessel such as vessel 48 shown in FIG. 6 with lowermost point P pointing downwardly and with upper points P1 and P2 suspended by the transducer assembly in a manner similar to that in which the parallelogram displacer 15 is suspended (see FIG. 8).

As with the above-described displacers, fluid height h may be expressed in terms of the reaction forces $F_1$ and $F_2$ exerted by the transducer assembly in response to corresponding buoyant force acting on the displacer 15a. It has been determined that for the displacer 15a, $$h = \frac{3F_2}{F_1 + F_2} \cdot H \qquad (7)$$

where $F_1$ and $F_2$ are the reaction forces (which are equal to the buoyant forces measured by the transducer assembly at corners P1 and P2), h is the fluid height, and H is the top to bottom height of the displacer 15a. Additional equations for high or low fluid levels and for liquid density may be generated as described above with respect to the displacers 10, 12 and 15.

Although only three embodiments of the invention have been shown and described, further modifications and rearrangements of the components of the fluid parameter monitoring device will be apparent to those skilled in the art. The present invention is not intended to be limited to the embodiments described herein, but is instead defined only by the appended claims.

What is claimed is:

1. An apparatus for measuring characteristics of a fluid contained in a vessel, said apparatus comprising:
   a first fluid displacer having cross-section which varies with depth in the vessel and having a shape such that when the first fluid displacer is positioned in the vessel, buoyant force exerted by the fluid on the first fluid displacer depends on the level of the fluid;
   a second fluid displacer having cross-section which varies with depth in the vessel and having shape such that when the second fluid displacer is positioned in the vessel, buoyant force exerted by the fluid on the second fluid displacer depends on the level of the fluid;
   a first force transducer coupled to the first fluid displacer;
   a second force transducer coupled to the second fluid displacer; and
   processing means coupled to the first force transducer and to the second force transducer for receiving a first signal from the first force transducer and a second signal from the second force transducer, the first signal and the second signal being indicative of fluid forces acting on the first fluid displacer and the second fluid displacer, and for processing the first signal and the second signal to generate at least one signal indicative of at least one characteristic of the fluid.

2. The apparatus of claim 1 wherein each of the first fluid displacer and the second fluid displacer is a substantially triangle-shaped fluid displacer, the first fluid displacer is coupled to the first force transducer in an upright orientation, and the second fluid displacer is coupled to the second force transducer in an inverted orientation.

3. An apparatus for measuring characteristics of a fluid contained in a vessel, the fluid having a level in the vessel and a density, the apparatus comprising:
   a first fluid displacer having cross-section which varies with depth in the vessel and shape such that when the first fluid displacer is positioned in the vessel, buoyant force exerted by the fluid on the first fluid displacer depends on the level;
   a second fluid displacer having cross-section which varies with depth in the vessel and shape such that when the second fluid displacer is positioned in the vessel, buoyant force exerted by the fluid on the second fluid displacer depends on the level;
   a first force transducer coupled to the first fluid displacer and a second force transducer coupled to the second fluid displacer; and
   a processing means coupled to the first force transducer and to the second force transducer for receiving a first signal from the first force transducer and a second signal from the second force transducer, the first signal and the second signal being indicative of fluid forces acting on the first fluid displacer and the second fluid displacer, said processing means being configured to process the first signal and the second signal in accordance with simultaneous expressions relating said first signal and said second signal to the level and the density to generate a signal indicative of the level and a signal indicative of the density.

4. The apparatus of claim 3, also including a temperature monitoring device coupled to the processing means, and wherein the processing means is configured to receive a third signal from the temperature monitoring device while said temperature monitoring device monitors the fluid and to process the third signal to generate a signal indicative of temperature of the fluid.

5. The apparatus of claim 4, wherein the processing means is also configured to process the first signal, the second signal, and the third signal to generate a signal indicative of solute concentration in the fluid.

6. The apparatus of claim 3, wherein each of the first fluid displacer and the second fluid displacer is a substantially triangle-shaped fluid displacer.

7. The apparatus of claim 6, wherein the first fluid displacer is coupled to the first force transducer in an upright orientation and the second fluid displacer is coupled to the second force transducer in an inverted orientation.

8. The apparatus of claim 3, wherein each of the first fluid displacer and the second fluid displacer has at least a substantially triangular shape, and wherein the simultaneous expressions are $$h = H \cdot \left( 1 - k_1 \cdot \frac{F_\Delta - F_\nabla}{F_\Delta + F_\nabla} \right)$$

and $$\rho = \frac{F_\Delta + F_\nabla}{K_2 g} \left( H - H k_1 \left( \frac{F_\Delta - F_\nabla}{F_\Delta + F_\nabla} \right) \right)^{-1}$$

where $\rho$ is the density, $F_\Delta$ is the buoyant force exerted by the fluid on the first fluid displacer, $F_\nabla$ is the buoyant force exerted by the fluid on the second fluid displacer, g is the gravitational constant, $k_1$ is a dimensionless constant determined by shape of the first fluid displacer and the second fluid displacer, $k_2$ is another dimensionless constant determined by shape of the first fluid displacer and the second fluid displacer, each of the first fluid displacer and the second fluid displacer has a top and a bottom separated by a distance, and "H" is the distance between the top and the bottom.

9. The apparatus of claim 8, wherein each of the first fluid displacer and the second fluid displacer has a rectangular small face, each of the first fluid displacer and the second fluid displacer has a rectangular large face, the rectangular small face has width "a" and depth "c", the rectangular large face has width "b" and depth "c," $k_1=a+b/(b-a)$, $k_2=c(a+b)$, and "H" is the distance between the rectangular small face and the rectangular large face.

10. The apparatus of claim 3, wherein the simultaneous expressions are $$h = H \cdot \left( 1 - k_1 \cdot \frac{F_\Delta - F_\nabla}{F_\Delta + F_\nabla} \right)$$

and $$h = \frac{F_\Delta + F_\nabla}{k_2 \rho g}$$

where ρ is the density, "h" is the level, "g" is the gravitational constant, $F_\Delta$ is the buoyant force on the first fluid displacer, $F_\nabla$ is the buoyant force on the second fluid displacer, g is the gravitational constant, $k_1$ is a dimensionless constant determined by shape of the first fluid displacer and the second fluid displacer, $k_2$ is another dimensionless constant determined by shape of the first fluid displacer and the second fluid displacer, each of the first fluid displacer and the second fluid displacer has a top and a bottom separated by a distance, and "H" is the distance between the top and the bottom.

11. The apparatus of claim 10, wherein each of the first fluid displacer and the second fluid displacer has a rectangular small face, each of the first fluid displacer and the second fluid displacer has a rectangular large face, the rectangular small face has width "a" and depth "c", the rectangular larger face has width "b" and depth "c," $k_1=a+b/(b-a)$, $k_2=c(a+b)$, and "H" is the distance between the rectangular small face and the rectangular large face.

12. An apparatus for measuring fluid density and fluid cascading, said apparatus comprising:

first, second and third fluid displacers, the first and second fluid displacers being of at least substantially triangular cross-section;

first, second and third force transducers coupled to the first, the second, and the third fluid displacers, respectively;

processing means coupled to the first, the second, and the third force transducers for receiving first and second signals representing buoyant forces acting on the first and the second fluid displacers and a third signal representing cascading forces acting on the third fluid displacer, and configured to process the first, the second, and the third signals to generate a signal indicative of fluid density and an additional signal indicating the presence or absence of cascading fluid.

13. The apparatus of claim 12 wherein the processing means is configured to process the first and second signals to generate a signal indicative of fluid level in addition to said signal indicative of fluid density.

14. The apparatus of claim 12, also including a temperature monitoring device coupled to the processing means, and wherein the processing means is configured to receive a fourth signal from the temperature monitoring device while said temperature monitoring device monitors a fluid and to process the fourth signal to generate a signal indicative of temperature of the fluid.

15. The apparatus of claim 14, wherein the processing means is configured to process the first signal, the second signal, and the signal indicative of the temperature of the fluid to generate a signal indicative of solute concentration in the fluid.

16. The apparatus of claim 12, wherein the first fluid displacer is coupled to the first force transducer in an upright orientation and the second fluid displacer is coupled to the second force transducer in an inverted orientation.

17. A method of monitoring fluid parameters which comprises the steps of:

(a) measuring fluid forces acting upon at least a first fluid displacer and a second fluid displacer suspended in a fluid, each of the first fluid displacer and the second fluid displacer having cross-section which varies with depth in the fluid; and (b) processing a first signal indicative of the measured fluid forces on the first fluid displacer and a second signal indicative of the measured fluid forces on the second fluid displacer in accordance with simultaneous expressions relating said first signal and said second signal to level of the fluid and density of the fluid to generate a signal indicative of the level and a signal indicative of the density.

18. The method of claim 17 wherein the fluid forces measured during step (a) are buoyant forces.

19. The method of claim 17, wherein each of the first fluid displacer and the second fluid displacer is a substantially triangle-shaped fluid displacer.

20. The method of claim 19, wherein during step (a), the first fluid displacer is positioned in the fluid in an upright orientation, and the second fluid displacer is positioned in the fluid in an inverted orientation.

21. The method of claim 17, wherein the first fluid displacer and the second fluid displacer are suspended in the fluid in a vessel, and also including the steps of:

measuring a cascading force acting upon a third fluid displacer; and processing the first signal, the second signal, and a signal indicative of the measured cascading force to generate a signal indicative of fluid flow from the vessel.

* * * * *